(12) United States Patent
Bruun-Jensen et al.

(10) Patent No.: US 8,465,153 B1
(45) Date of Patent: Jun. 18, 2013

(54) SYSTEM FOR CLINICAL EXAMINATION OF VISUAL FUNCTIONS USING LENTICULAR OPTICS OR PROGRAMMABLE DISPLAYS

(76) Inventors: Joergen Bruun-Jensen, Slagelse (DK); Jacob Bruun-Jensen, Marlow (GB)

( * ) Notice: Subject to any disclaimer, the term of this patent is extended or adjusted under 35 U.S.C. 154(b) by 0 days.

(21) Appl. No.: 13/247,320

(22) Filed: Sep. 28, 2011

Related U.S. Application Data

(60) Provisional application No. 61/416,375, filed on Nov. 23, 2010.

(51) Int. Cl.
*A61B 3/00* (2006.01)
*A61B 3/02* (2006.01)
*G03B 21/60* (2006.01)

(52) U.S. Cl.
USPC ............ 351/232; 351/200; 351/222; 359/455

(58) Field of Classification Search
USPC ................ 351/232, 222, 200, 201, 239, 240, 351/237, 245–246; 359/618–621, 625–626, 359/443, 454–455
See application file for complete search history.

(56) References Cited

U.S. PATENT DOCUMENTS

| | | | | |
|---|---|---|---|---|
| 3,785,723 | A * | 1/1974 | Guyton | 351/241 |
| 2004/0061775 | A1 * | 4/2004 | McCoy et al. | 348/42 |
| 2008/0316428 | A1 * | 12/2008 | Oda | 351/240 |
| 2010/0283969 | A1 * | 11/2010 | Cooperstock et al. | 351/201 |

* cited by examiner

*Primary Examiner* — Dawayne A Pinkney
(74) *Attorney, Agent, or Firm* — Steven M. Hoffberg; Ostrolenk Faber LLP

(57) ABSTRACT

A system having one or more lenticular units and more supplementary parts without lenticular properties. The lenticular units consist of lenticular plates that are capable of visualizing various clinically relevant examination objects. In all the examination positions, the system may visualize a fixation area that is shown alone or together with clinically relevant examination objects targeted at the examination of clinically relevant visual functions. Supplementary parts with various optical properties may be fixed or be moved relative to the lenticular units. Various clinically relevant examination objects may be visualized for the right eye and the left eye in that the examination objects of the system are provided with different colors or light polarizations and using eyeglasses with a differently colored glass for the right eye and the left eye or with polarization filters with a different direction for the right eye and the left eye.

20 Claims, 15 Drawing Sheets

SCOTOMA

METAMORPHOPSIA

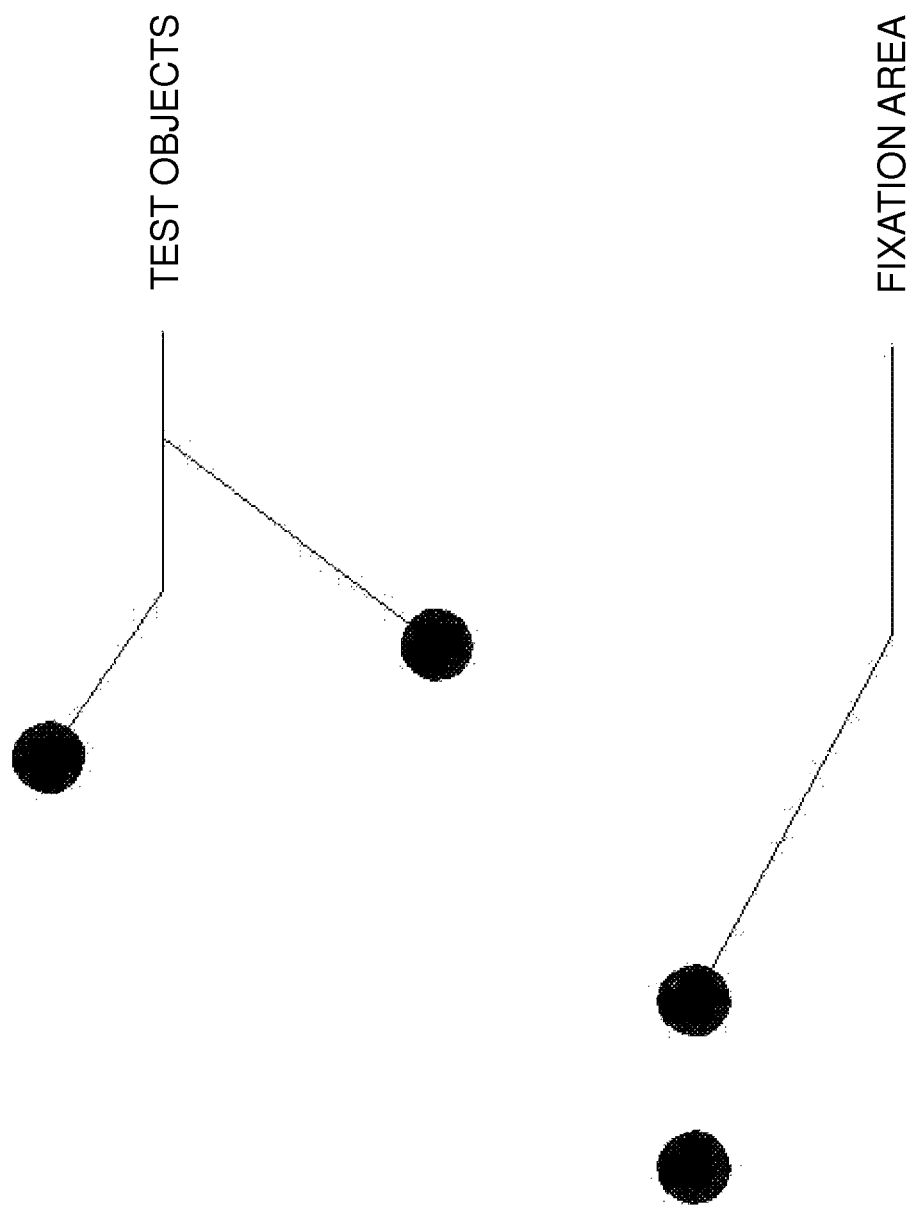

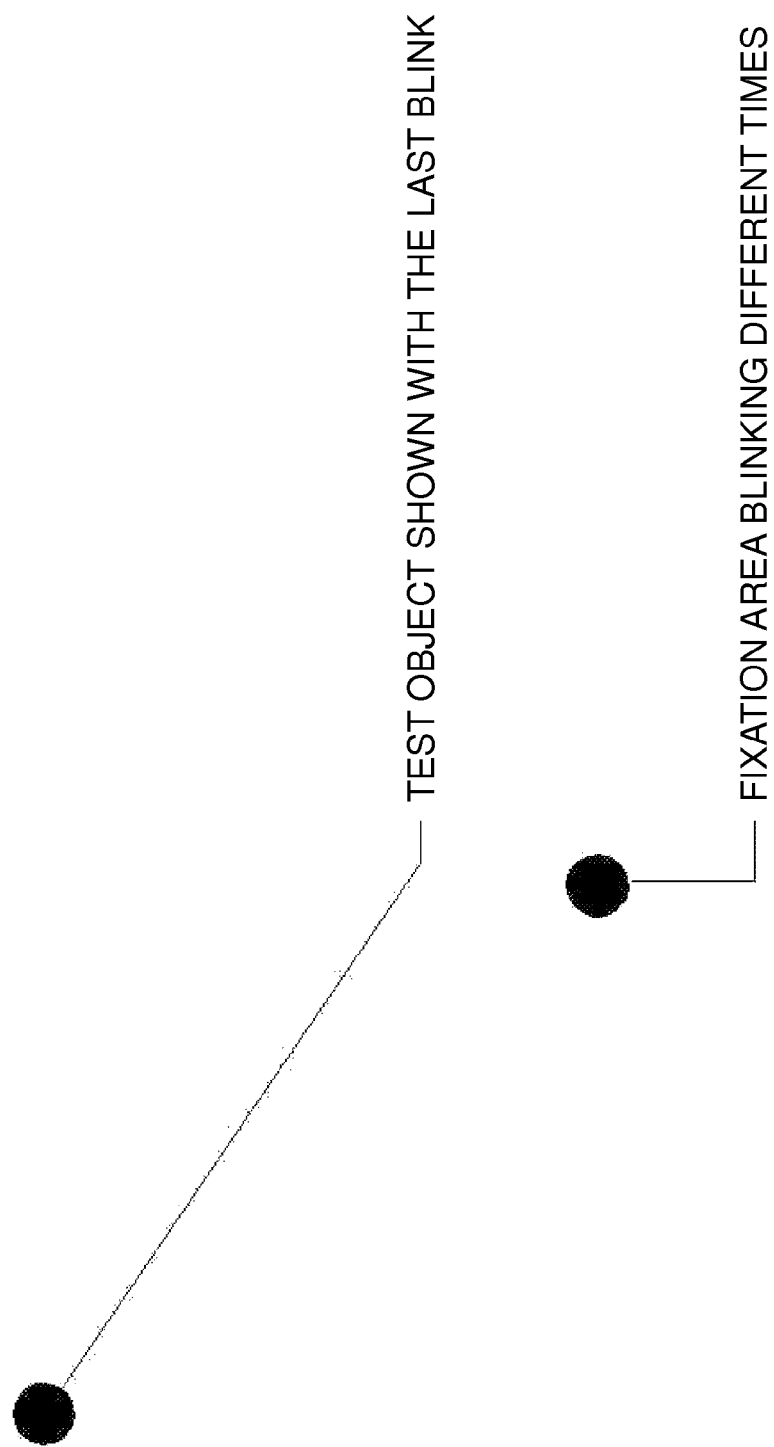

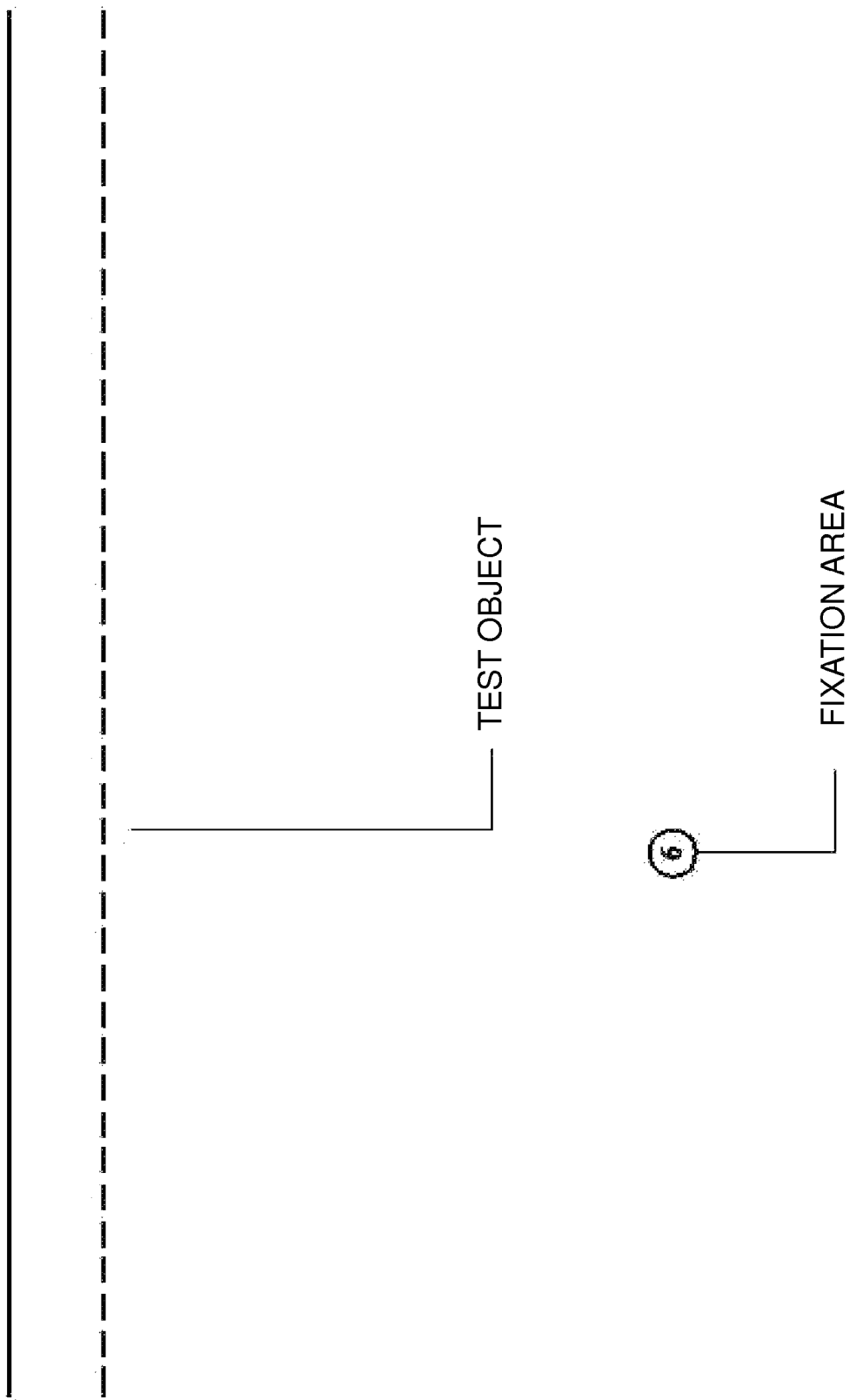

METAMORPHOPSIA

SCOTOMA

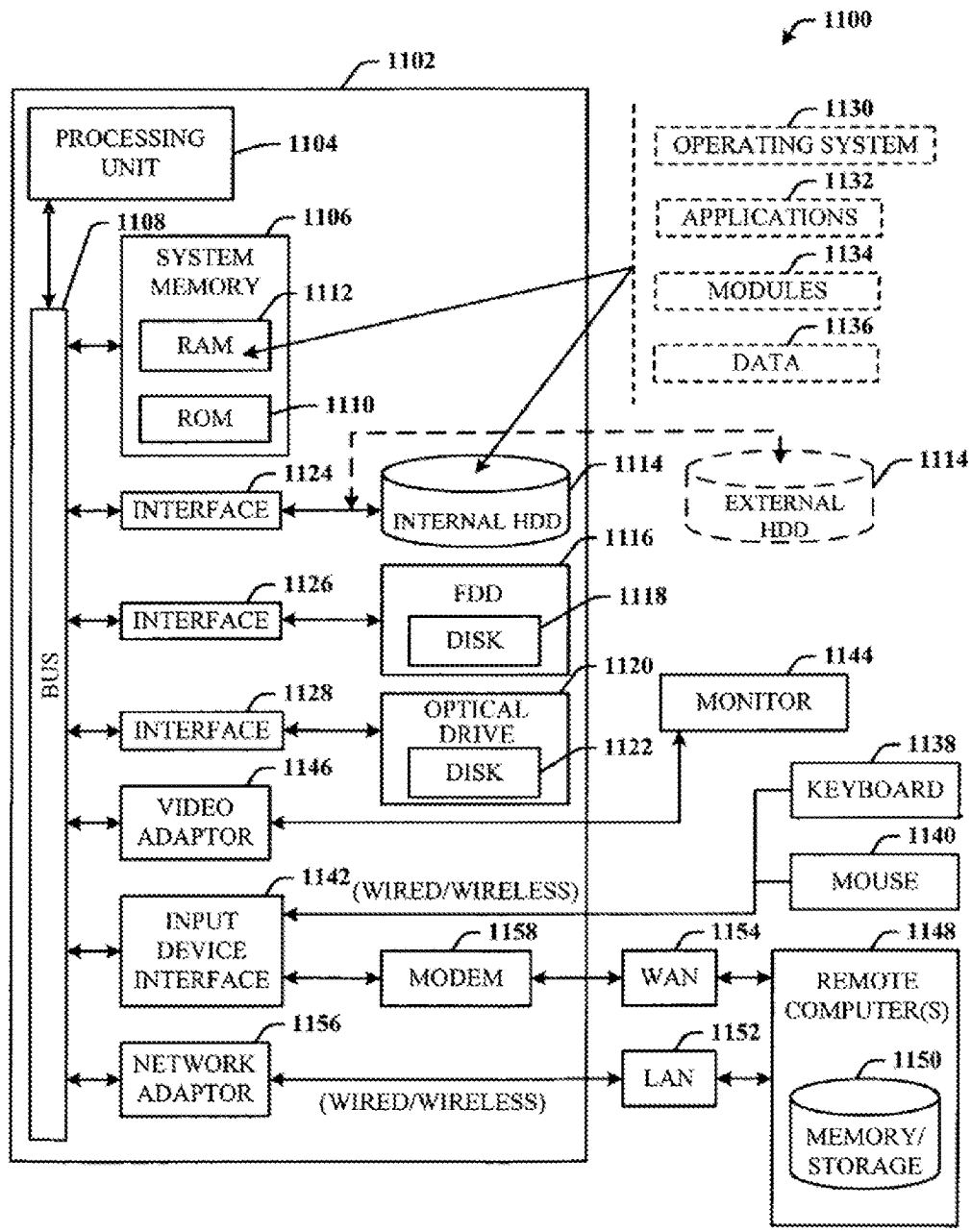
Fig. 15 – Prior Art

SYSTEM FOR CLINICAL EXAMINATION OF VISUAL FUNCTIONS USING LENTICULAR OPTICS OR PROGRAMMABLE DISPLAYS

FIELD OF THE INVENTION

The present invention relates to a system, which may be used for functional examination of scotoma and metamorphopsia in the monocular or binocular visual functions with a view to early detection and control of pathological changes in the visual system.

BACKGROUND OF THE INVENTION

Visual acuity is typically measured with a functional test of the most central part in the visual system, and relates to the function of fovea of the retina and the nerve and brain function related to this area. Many early diseases of the visual system do not change the visual acuity, but rather change the function in smaller or larger areas of the visual field or change the binocular vision. There is often a significant discrepancy between objective tests, visual acuity and function in the visual field.

The most common eye diseases affecting the central visual field are Age Related Maculopathy, Diabetic Retinopathy and Glaucoma. To discover and to follow treatment of these eye diseases are utmost important.

Among doctors, ophthalmologists, opticians and other individuals who perform examinations of visual functions, there is an unmet need with respect to the ability of examining clinically relevant visual functions in the central visual field and binocular vision by means of simple methods. In addition, there is a need for self-examination among people who have an increased risk of diseases in retina, visual pathways and brain, and among patients who have previously had diagnosed such diseases and are at risk of progression. If these patients themselves have the possibility of discovering early pathological, functional changes in the visual system, or discovering important clinical changes detected previously, prevention or treatment may be initiated quicker and with better results.

Visual functions that may advantageously be examined comprise:
the visual field from 0 to 10 degrees
the visual field from 10 to 25 degrees
Binocular visual functions.

The central part of the visual field within a distance of 10 degrees from the center corresponds to most of the macular area in the central part of the retina of the eye. Some visual functions in this area may be affected in different ways by diseases in the macular area of the retina (maculopathy) or by changes in front of or below this area of the retina. These diseases may involve small defects (scotomas) in the visual field (FIG. 1), because sensory cells, nerve cells or nerve threads in this area have ceased or depressed function. In addition, changes in the microstructure of the retina or other impact on the sensory cells of the retina may occur. This may result in metamorphopsia (FIG. 2), where straight lines are seen as broken, bent, wavy, vibrating, twisted or colored lines. Metamorphopsia is a typical symptom, which can often be related to functional disturbances in the retina. The visual perception of scotomas and metamorphopsia is modulated by dynamic changes in the plasticity of the brain.

Some of the causes of functional changes in the macular area in the form of scotomas and metamorphopsia may be membranes or obscurities in front of parts of the macula. Holes in the retina, oedema, bleeding, inflammation, toxic impact, tumor formation or membrane formation and in-growth of new blood vessels (neovascularization) in the macula or just below the macula (subretinal neovascular membranes) may be other causes.

Pathological visual functions in the visual field from 10 to 25 degrees may be caused by glaucoma, diseases in the retina, visual nerves, and visual pathways and in the brain.

Pathological binocular functions may occur, if the visual development does not proceed normally, after traumas, pathological changes in eyes and eye surroundings, chemical impacts, or diseases which affect the normal control and regulation of the binocular vision.

Known Examination Systems

With various forms of visual field examination (perimetry), it is possible to examine various parts of the visual field. To this end, computer-controlled, high-technological instruments (automatic perimetry), which lend themselves to stationary use, are frequently employed. Functional impairment or functional cessation in some areas of the visual field may be detected with these instruments. But, it is not possible to detect the special changes in the form of metamorphopsia (FIG. 2) in this manner.

Preferential Hyperacuity Perimeter (Carl Zeiss Meditec) U.S. Pat. No. 6,656,131, expressly incorporated herein by reference, uses a computer and a monitor, it being possible with hyperacuity objects to detect metamorphopsia in the central and paracentral areas of the macula. This method requires relatively costly and stationary equipment.

In 1947, Marc Amsler introduced various charts for the examination of the central visual field within 10 degrees. The chart most used has a 100 mm square field, which is divided by vertical and horizontal lines that form 400 squares of 5 mm each. The lines may be black on a white background, white lines on a black background or colored lines on a white, dark or colored background. In the monocular examination, the chart is held at a distance of 30 cm from the eye, so that each square corresponds to 1 degree of the visual field. The center of the chart includes a fixation point, which the patient is to fixate constantly. In use, the patient tries to indicate whether all lines and squares can be seen, or can be seen with the same clarity, or whether there are lines which are perceived as broken, bent, wavy or twisted lines. Then, the patient tries to draw the seen changes on the chart.

See Also, (WO/2010/023470) Ophthalmic Diagnostic Apparatus, (WO/2008/020252) Ophthalmic Diagnostic Apparatus, (WO/2004/000108) Computer-Based Visual Field Testing, (WO/2003/092481) Characterization Of Visual Field Defects, (WO/2003/070089) Method And System For Assessing Eye Disease, (WO/2003/061521) Methods And Apparatus For Observing And Recording Irregularities Of The Macula And Nearby Retinal Field, (WO/2003/028534) System And Method For Full Field Oscillating Stimulus Perimeter, (WO/2002/028266) Methods Devices And Systems For Detecting Eye Disease, (WO/2002/005704) Virtual Reality Peripheral Vision Scotoma Screening, (WO/2001/072212) Computer-Based 3d Visual Field Test System And Analysis, (WO/1999/026524) Method And Apparatus For Measuring And Correcting Metamorphopsia, (WO/1998/017168) A Method Of Corneal Analysis Using A Checkered Placido Apparatus, (WO/1997/024058) Ophthalmological Self-Test Unit For Evaluating Macular Degeneration, (WO/1996/034555) Method And Apparatus For Central Visual Field Mapping And Optimization Of Image Presentation Based Upon Mapped Parameters, (WO/1996/032880) Automated Pocket-Sized Near Vision Tester, (WO/1987/004264) System And Method Of Detecting Visual Field Defects, US Application Nos. 20090273758, 20090231545, 20090143685, 20090109399, 20080309879, 20080309878, 20080137036, 20070268455, 20070200927, 20050261557, 20050122477, 20040193070, 20040125341, 20040075814, 20040046934, 20030223038, 20030212310, 20030117582, 20030081176, 20030020873, 20030002014, 20020042580, 20020024634, 20010055095, U.S. Pat. Nos. 7,771,051, 7,425,067, 7,614,746, 7,275,830, 7,220,000, 7,101,044, 6,769,770, 6,742,894, 6,736,511, 6,656,131, 6,585,376, 6,578,966, 6,494,578, 6,450,641, 6,213,605, 6,108,634, 5,892,570 5,883,692, 5,841,511, 5,838,422, 5,646,710, 5,596,379, 5,589,897, 5,880,814, 5,568,209, 5,416,540, 5,139,030, 5,121,981, 4,826,308, 4,818,091, 4,798,456, each of which is expressly incorporated herein by reference.

The clinical use of Amsler charts involves various problems:
a) Many people have difficulty in maintaining the central fixation, habitually or because of a central scotoma. When they move the fixation to other locations on the chart, then small changes in the lines of the squares are not discovered, or they are registered wrongly.
b) It is difficult for many people to mark the changes, which they see on the chart.
c) When a person has fixated a few seconds on the fixation point, then the brain begins to modulate in the visual field. The constant fixation and all the many squares and lines trigger crowding (multiple lines in the grid interfere with the perception), perceptual fading (Troxler effect where perifoveal stimuli fade or disappear), perceptual filling in (scotoma become replaced by their background and small defects in straight lines are completed) and hyperacuity (displaced lines are aligned). This means that some scotomas and metamorphopsia cannot be discovered, and that the sensitivity of the examination is reduced significantly.

Various methods have been developed to reduce these problems of examinations with Amsler charts. The PCT application WO 87/04264 A1 (System and method of detecting visual field defects), expressly incorporated herein by reference, discloses a method using eyeglasses having a pair of cross-polarizing lenses, which may be varied selectively, so that the Amsler chart may be seen with different luminance, thus increasing the sensitivity of the examination. In the U.S. Pat. No. 5,646,710 (Ophthalmological self-test for evaluation of macular degeneration), expressly incorporated herein by reference, the Amsler chart is provided with a magnetic rear face so that it may be applied to a metallic surface, and may moreover be provided with a central fixation object consisting of a light source. The PCT application WO 99/26524 A1 (Method and apparatus for measuring and correcting metamorphopsia), expressly incorporated herein by references, uses a computer and a monitor on which an Amsler grid may be displayed. With a computer mouse, the patient is able to control a cursor and indicate the areas where parts of the grid cannot be seen (scotoma). If the patient discovers deformations of the grid (metamorphopsia), the cursor may be controlled to adjust these areas, so that all the lines in the grid become straight. All markings are stored in the computer and may be compared with subsequent examinations.

U.S. Pat. No. 6,585,376 (Test charts for metamorphopsia) expressly incorporated herein by reference, discloses a method of quantifying metamorphopsia in a horizontal and a vertical direction close to the fixation point. The method consists of different charts, where one or two fixation points, a white line or a straight row of white circular dots are printed on a black background. Metamorphopsia may be quantified by increasing the size of the dots and the distance between them.

The document US 2004/0061775 A1 discloses a digital binocular fusing apparatus where a stationary lenticular lens array produces a secondary 3D image from a primary image on a display mounted behind the lens array. The display could be a liquid crystal display or another electronic display, which are capable of producing and controlling pixels. The apparatus is designed to produce 3D images and enable visual presentation of video games and movies without using special eyeglasses or other optical apparatus adjacent the eyes of a viewer.

The document EP 0 830 839 A2 discloses a digital binocular view function inspecting apparatus for measuring the strabismus angle. A reference image for one eye and an index image for the other eye are displayed on a 3D display device. The person to be inspected can with the help of a computer mouse move the index image until the person visually recognizes the two images coincide. The computer calculates the actual amount of deviation between the two images. The document discloses that the 3D display could be a display of the parallax barrier type or of the lenticular type. The 3D display is a stationary one.

The document WO 03/092482 A1 discloses an ocular display apparatus for assessment and measuring of and for treatment of ocular disorder. The apparatus having image presentation means adapted to display a first image to one eye only of a subject, and a second, different image to the subject's other eye only so that the subject perceive a composite image including a moving object.

The apparatus is capable of presenting images to the subject on a split screen or on two separate screens. The images are perceived as 2D or 3D images. The display screens are stationary.

The document JP 2001 340300 A discloses a pupil detection device and a method of detecting the pupil position, and a 3D image display system, which use a stationary crossing lenticular system, and infrared light for detecting.

SUMMARY AND OBJECTS OF THE INVENTION

Many diseases in the visual system only affect one eye or affect both eyes differently. Clinical examination of the visual field depends on:
examination objects and presenting time
stable central fixation
illumination and background
correction for distance and refraction anomalies
the viewer's visual attention and psychophysical function.

It is very important to obtain a short presenting time of examination objects for visual field testing most particularly in the central part of the visual field. The present invention uses a non-texture background, shows the fixation area in all examination positions and shows a single or very few examination objects together with the fixation object for a very short interval of time (0.5-2.0 sec). In that way, the invention makes it possible to reduce the described visual problems of known examination methods, which apply similar principles to those of the Amsler grid.

The invention makes it possible to reduce the above-described visual problems of known examination methods, which apply the same principle as the Amsler grid. This is done by showing the fixation area in all examination positions and just showing a single or very few examination objects together with the fixation area for a very short interval of time (0.5-2.0 sec).

When observation direction, examination distance are changed, or the system is tilted or rotated to various positions, the fixation area is shown alone or together with one or more examination objects, which are targeted to examine clinical visual functions.

When switching between various observation directions with a very short time interval, problems of unstable fixation, crowding, filling-in and Troxler effect are reduced.

The examination possibilities, sensitivity and specificity of the system may be varied by using various lenticular units having various optical properties, using various clinically relevant examination objects, various positioning of clinically relevant examination objects, various contrast between background and examination objects and various optical properties of parts in front of or behind the lenticular unit.

In a simple embodiment, the invention may be produced at a relatively low price, thereby making it possible for many individuals to use the invention. In this manner, some pathological visual functions may be discovered timely, thereby providing for early diagnosis and treatment of the patient.

In various embodiments, the system may consist of one or more lenticular units and of one or more supplementary parts. Objects that are to be visible in all examination positions may be arranged on the rear face of a lenticular unit, on supplementary parts, in front of, or on, the front face of lenticular units, in areas of lenticular units where there are no lenticulars, or behind lenticular units at a distance where they are not affected by lenticular optics.

Fixation areas may be configured as a large or a small area, which may be unchanged in all examination positions, or may vary position and configuration in several of the examination positions of the system. Fixation areas may be black, white or colored.

The clinically relevant examination objects may be printed directly on the rear face, or on a plate, which is in contact with the rear side of the lenticular face. The graphical print may be divided by a special technique into narrow segments corresponding to the lenticular lenses, so that the same or different objects may be visualized by changing the observation direction or by tilting or rotating the system to various positions. The examination objects may be configured as images, drawings, geometrical elements, lines and rows or objects with the same or different numbers, shapes, sizes and with the same or different spaces. The objects may be white, grey, black or colored and have various positions in the various examination positions of the system.

Supplementary parts, which are arranged in front of or behind lenticular units, may be plates, which are provided with a different optical surface, light transparency, light polarization or color. These plates may be fixed or moved relative to the lenticular units.

In a preferred embodiment, the system has one or more examination positions and one or more recording positions. In examination positions, examination objects are shown for just a few seconds, typically 0.5 to 2.0 sec. In recording positions, the examination objects are shown together with elements in the form of lines, dots, squares, circles or colors which divide the examination objects into blocks or groups. Recording positions may be maintained for such a long time, typically 5.0 to 10.0 sec., that it is easier for the patient to indicate the changes that were discovered in the examination positions.

In other embodiments, the system may be used for examining some clinically relevant visual functions in various parts of the visual field. The system may be designed to examine with different sensitivity and specificity by using systems having different clinical, targeted properties. These systems may be provided with lenticular units having different functions, or supplementary plates having different optical properties and transparencies may be arranged in front of or behind the lenticular units. Further, it is possible to use fixation areas having different configurations and positions and examination objects of different numbers, positions, shapes, sizes and colors.

In other embodiments, the fixation area and examination objects may be displaced in various directions in various examination positions.

Both monocular and binocular examinations may be performed with the embodiments described. Using lenticular systems having 3D or zoom properties may perform special binocular examinations.

It is therefore an object to provide a system for clinical examination of visual system functioning comprising lenticular optics, a movable lenticular unit comprising one or more lenticular plates configured to project images of a plurality of different examination objects to a viewer dependent on an orientation of the lenticular unit with respect to the viewer along with a fixation area; and a holding part configured to orient and maintain an orientation of the lenticular unit in desired orientation with respect to the viewer. The system may further comprise at least one supplementary part configured to visually present an object having a predetermined position with respect to the lenticular unit. The lenticular unit may comprise a plurality of lenticular plates, each of the plurality of lenticular plates having a distinct lens structure. The examination objects may comprise a plurality of unique graphic icons. The system may further comprise an optically polarized plate, disposed between the viewer and the lenticular unit. The fixation area may have a predetermined position with respect to the examination objects in respectively different relative orientations of the lenticular unit with respect to the viewer. The examination objects may be provided in at least two different colors, and a set of color filter glasses provided for the viewer corresponding to at least two different colors. The system may further comprise eyeglasses having different light polarization for the right eye and the left eye of the viewer. The system may further comprise polarization filters, which are arranged such that the light projected to the viewer from the fixation area is not polarized, light projected from a first set of examination objects is polarized in a first direction, and light projected from a second set of examination objects is polarized in a second direction, and that eyeglasses with different light polarization permit visualization of the fixation area and the first set of examination objects by the left eye, and the fixation area and the second set of examination objects by the right eye of the viewer. It is also an object to provide a method for clinical examination of visual system functioning comprising providing a movable lenticular unit comprising one or more lenticular plates configured to project images of a plurality of different examination objects to a viewer dependent on an orientation of the lenticular unit with respect to the viewer along with a fixation area; orienting and maintaining an orientation of the lenticular unit in a desired orientation with respect to the viewer; and receiving a report of the visualization of the examination objects from the viewer. An object having a predetermined position with respect to the lenticular unit may be visually presented. The lenticular unit may comprise a plurality of lenticular plates, each of the plurality of lenticular plates having a distinct lens structure. The examination objects may comprise a plurality of unique graphic icons. An optically polarized sheet may be disposed between the viewer and the lenticular unit. The fixation area may have a predetermined position with respect to the examination objects in respectively different relative orientations of the lenticular unit with respect to the viewer. The examination objects may be provided in at least two different colors, further comprising viewing the examination objects through a set of color filter glasses corresponding to at least two different colors. Eyeglasses having different light polarization for the right eye and for the left eye of the viewer may be provided. Polarization filters may be arranged such that light projected to the viewer from the fixation area is not polarized, light projected from a first set of examination objects is polarized in a first direction, and light projected from a second set of examination objects is polarized in a second direction, and viewing the lenticular unit through eyeglasses with different light polarization which permit visualization of the fixation area and the first examination objects by the left eye, and the fixation area and the second examination objects by the right eye of the viewer.

BRIEF DESCRIPTION OF THE DRAWINGS

FIG. 7 shows an apparatus for investigation using one or more examination-objects and 1-2-3 points in the fixation area.

FIG. 8 shows a fixation area similar to FIG. 4, using dots blinking different times in the fixation area before examination-objects are shown.

FIG. 9 shows an examination object with a line and a row of dots.

FIG. 10 illustrates a scotoma and area with metamorphopsia.

FIG. 15 shows a block diagram of a computer system.

DETAILED DESCRIPTION OF THE PREFERRED EMBODIMENTS

Movable Lenticular Cards

The earliest lenticular techniques have been known since around 1940 and have subsequently been developed considerably and used for obtaining different binocular visual functions:

US 2004/0061775 A1 (Apparatus for placing primary image in registration with lenticular lens in system for using binocular fusing to produce secondary 3D image from primary image) is a digital binocular fusing apparatus where a stationary lenticular lens produces a secondary 3D image from the primary image on a display mounted behind the lens array and a primary image orientation adjustment system with sensors.

EP 0 830 839 A2 (Binocular view function inspecting apparatus and inspecting method) shows a system where a reference image for one eye and an index image for the other eye are displayed on a 3D display device. The person to be examined can move the index image until he or she visually recognizes the two images coincide. A computer calculates the amount of deviation between the two images.

JP 2001 340300 A (Pupil detecting device and method, fixation point detecting device and method, and three-dimensional image display system) uses a stationary crossing lenticular system and infrared light for detecting.

US 2008/0252718 A1 (Enhancement of visual perception) shows a system where a 2D image is enhanced by inducing a retinal disparity in the viewer that results in a fusion experience. An enhancer generates a virtual visually identical object by a holographic device, concave mirror projection device or with a lenticular device.

These systems use stationary lenticular devices in contrast to the present invention where movable lenticular cards are used to obtain short presenting time of examination objects.

A lenticular unit consists of a lenticular plate and rear face which is made by a special graphical technique such that, from this rear face, the lenticular plate is capable of showing clinically useful examination objects and fixation areas in the various examination positions of the system.

The lenticular plates may have the same or different optical properties. Lenticular plates may consist of one or more layers of rows of transparent, parallel lenses (lenticulars). Lenticular plates may be configured with the same or different lens shapes, lens sizes, numbers and densities of the lenses and in several layers, so that various optical properties may be provided by the system.

Figure 1:
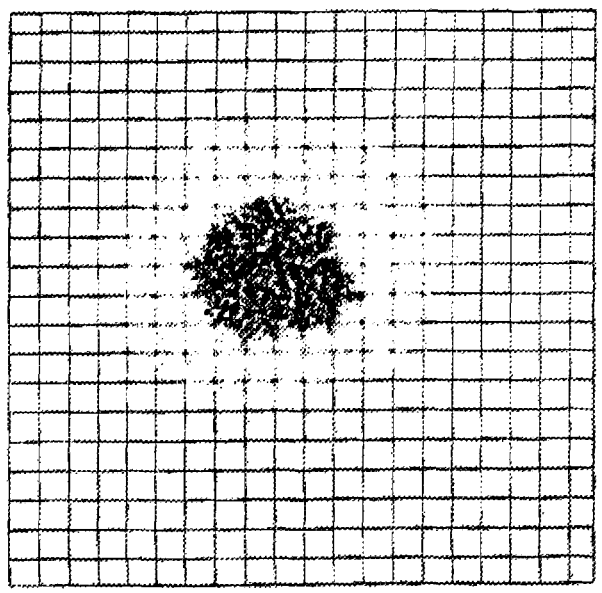
FIG. 1 shows a drawing of scotoma marked on an Amsler chart.
Figure 2:
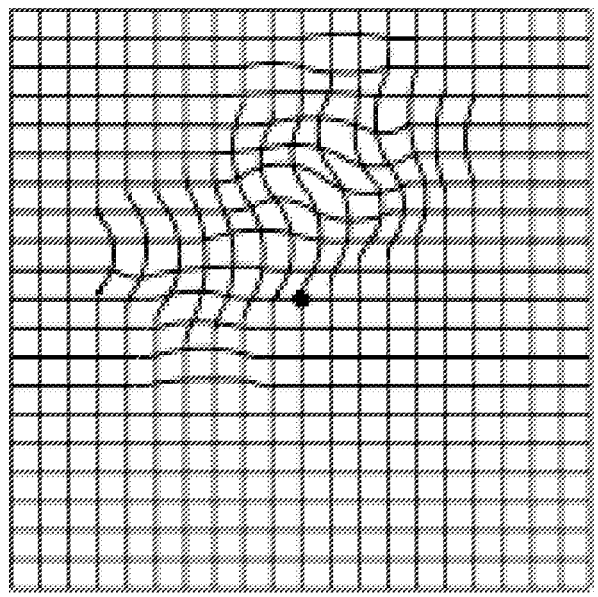
FIG. 2 shows a drawing of metamorphopsia marked on an Amsler chart.
Figure 3:
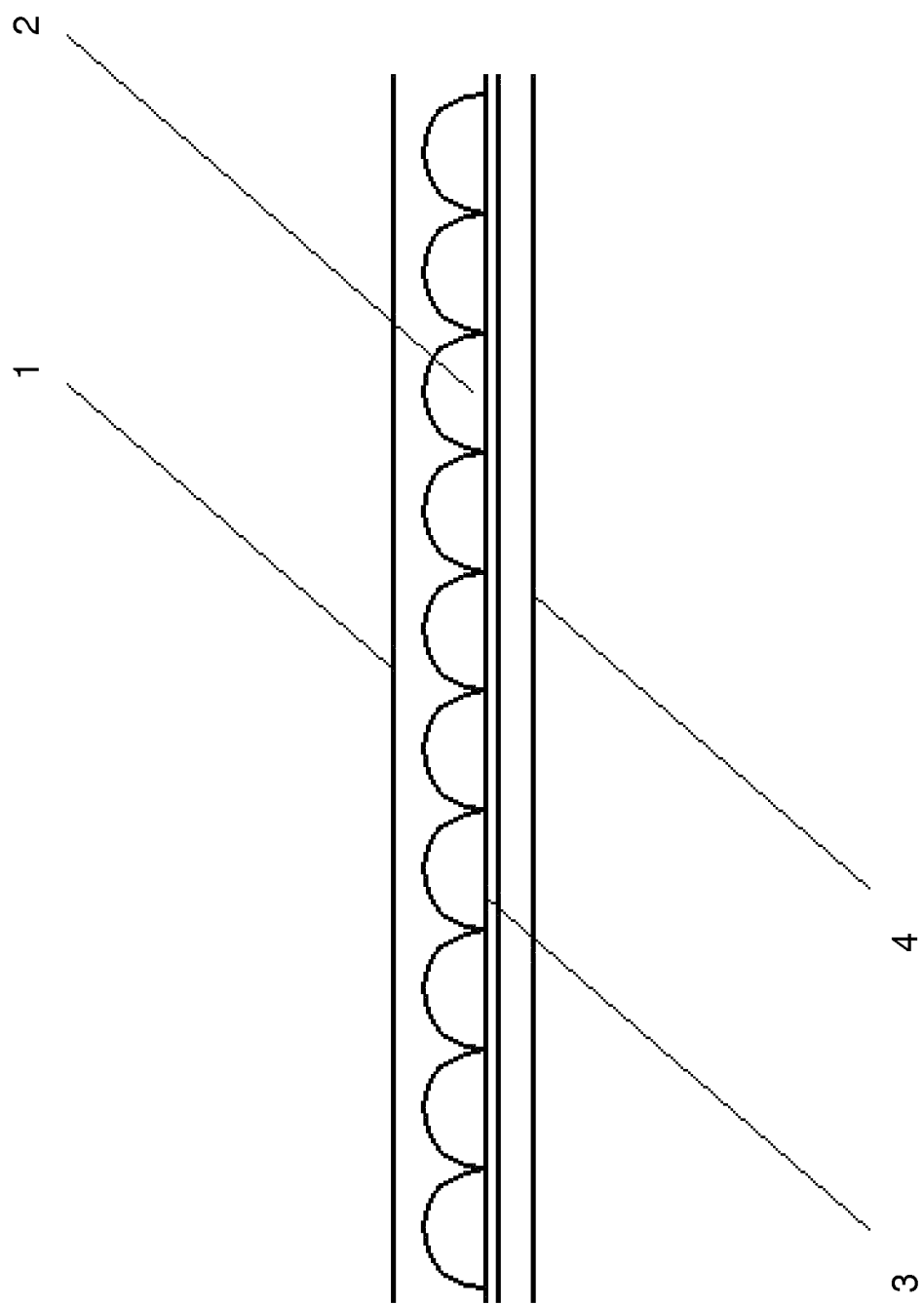
FIG. 3 shows a sectional drawing of the system perpendicular to the longitudinal direction of the lenses in the lenticular face.

The clinically useful examination objects may be printed directly on the rear face, or on a plate (FIG. 3), which is in contact with the rear side of the lenticular face. The graphical print may be divided by a special technique into narrow segments corresponding to the lenticular lenses, so that the same or different objects may be visualized by changing the observation distance, observation direction, or by tilting or rotating the system to various positions.

That is, the lenticular card may be provided in which the fixation area which is visible over a wide range of viewing angles, with different examination patterns selectively visible in different viewing positions, while fixing gaze on the always visible fixation area. Thus, the virtual movement or reconfiguration of the examination patterns is possible by shifting the angle of a relatively simple examination card.

When observation direction, examination distance are changed, or the system is tilted or rotated to various positions, the fixation area is shown alone or together with one or more examination objects, which are targeted to examine clinical visual functions. When switching between various observation directions with a very short interval of time, problems of unstable fixation, crowding, filling-in and Troxler effect may be reduced according to the invention.

The examination possibilities, sensitivity and specificity of the system may be varied by using various lenticular units having various optical properties, using various examination objects, various positioning of examination objects, various contrast between background and examination objects and various optical properties of parts in front of or behind the lenticular unit.

In the present invention one embodiment constitutes a system of one or more lenticular units provided on cards, and of supplementary parts, which are necessary for the use of the system.

Supplementary Parts

The supplementary parts, which generally do not have lenticular structures, may consist of one or more mounting parts, holders and couplings, for which one or more lenticular units are arranged. Mounting parts may have the same or different colors and different transparencies to light.

The supplementary parts may moreover consist of plates, which are disposed in front of and behind the lenticular units. These plates may be more or less transparent to light, have different colors and different light polarizations.

A fixation area having the same or a movable position relative to the lenticular units may be applied to the supplementary parts.

The mounting parts may, for example, hold the card in a stable manner such that the angle of gaze, and thus the intended examination pattern, can be controlled and changed. For example, a card mount may have a telescoping or deployable end (such as a tape measure), to help ensure the correct working 12 inches distance, and define the normal angle to the nose. The card is supported by a clamp at the base of the deployable end, having a set of angular detents. In a typical case, the printing behind the lenticular screen will have 15 degree offset viewing angles, and provide eight superposed images. The angular detents are therefore provided at 15-degree intervals. The locking force need not be high. For example poled flexible ceramic magnets slipping against each other could create such forces. The supplementary parts, such as a fixation object, may extend from the clamp or element close to the clamp.

In various embodiments, the system may consist of one or more lenticular units and optionally of one or more supplementary parts. Objects which are to be visible in all examination positions (FIG. 3), may be arranged on the rear face of a lenticular unit, on supplementary parts, in front of (1) the face of lenticular units (2), in areas of lenticular units where there are no lenticulars, or behind lenticular units (4) at a distance where they are not affected by lenticular optics.

Supplementary parts (FIG. 3), which are arranged in front of (1) or behind (4) lenticular units (2), may be plates which are provided with a different optical surfaces, light transparency, light polarization or color. These plates may be fixed or moved relative to the lenticular units.

In an embodiment, the system has one or more examination positions and one or more recording positions. In examination positions, examination objects are shown for just a few seconds, typically 0.2 to 0.5 sec. In recording positions, the examination objects are shown together with elements in the form of lines, dots, squares, circles or colors which divide the examination objects into blocks or groups. Recording positions may be maintained for such a long time, typically 5.0 to 10.0 sec., that it is easier for the patient to indicate the changes, which were discovered in the examination positions.

In other embodiments, the system may be used for examining some clinically relevant visual functions in various parts of the visual field. The system may be designed to examine with different sensitivity and specificity by using systems having different clinical, targeted properties. These systems may be provided with lenticular units having different functions, or supplementary plates having different optical properties and transparencies may be arranged in front of or behind the lenticular units. Further, it is possible to use fixation areas having different configurations and positions and examination objects of different numbers, positions, shapes, sizes and colors. In other embodiments, the fixation area and examination objects may be displaced in various directions in various examination positions.

Both monocular and binocular examinations may be performed with the embodiments described.

Fixation Area and Examination Objects

Attention to the Fixation Area

In automatic perimetry, clinically relevant examination objects are shown between 0.5-2.0 seconds in different parts of the visual field. In that way the patient's eye or eyes cannot react to shift from the central fixation area. This method could be improved by constantly observing the patient's fixation and vocally correcting the patient if the fixation shifts. An eye-tracking system may also be used.

Figure 4:
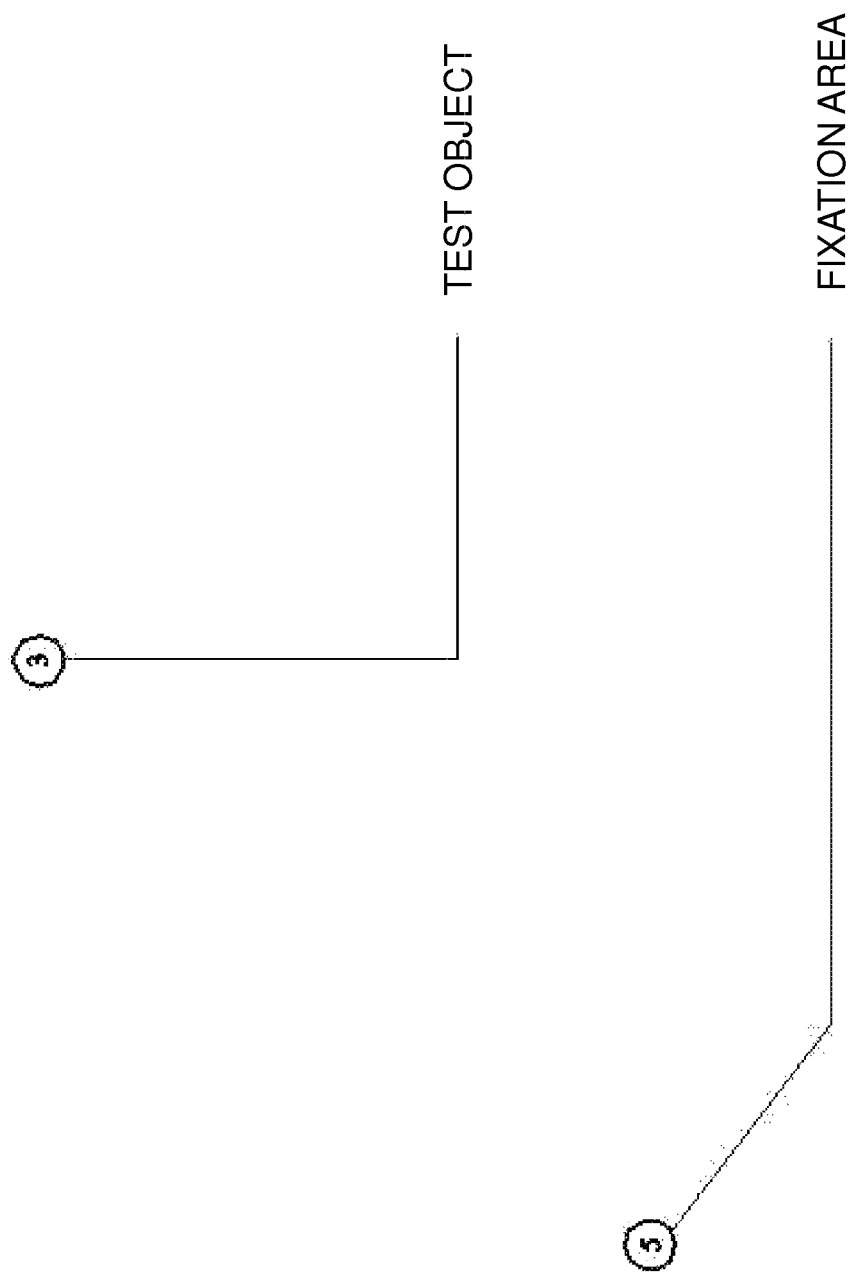
FIG. 4 shows a fixation area and examination object integrated using numbers in circles.
Figure 5:
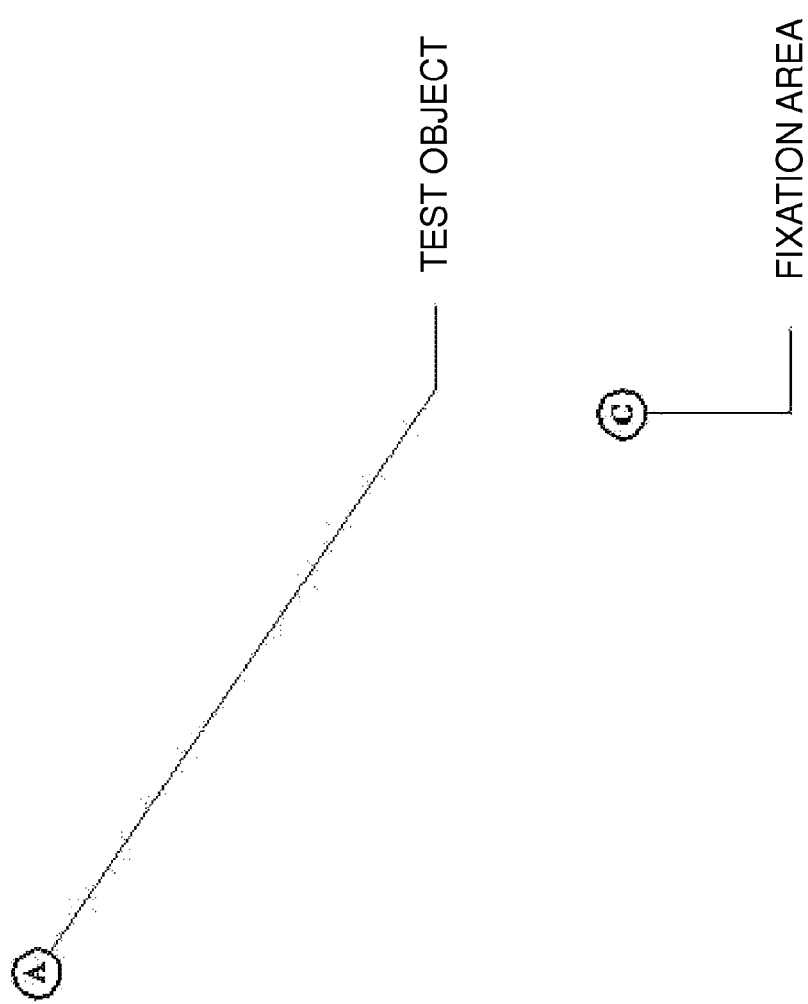
FIG. 5 shows a fixation area similar to FIG. 4, using characters.

To have a higher degree of attention to the fixation area and get a stable fixation, examination objects are placed in the fixation area and integrated with the examination objects in the visual field. FIG. 4 shows such a system: Both the fixation area and the examination object consist of a circular ring and inside the ring is a number. The examination object and the number in the fixation area are displayed together very shortly. The ring in the fixation area is shown constantly. Every time a new examination object is shown it has a different number in the ring and the ring in the fixation area has a new number. The patient has to read all the numbers aloud for notation by an observer, or otherwise to transcribe it or input it into a digital system. Instead of numbers, characters could be used as shown in FIG. 5. The system is useful as an indicator for visual attention. Preferably, the number, letters or images do not follow a predicable order, so that the user cannot infer a missing examination object.

Figure 6:
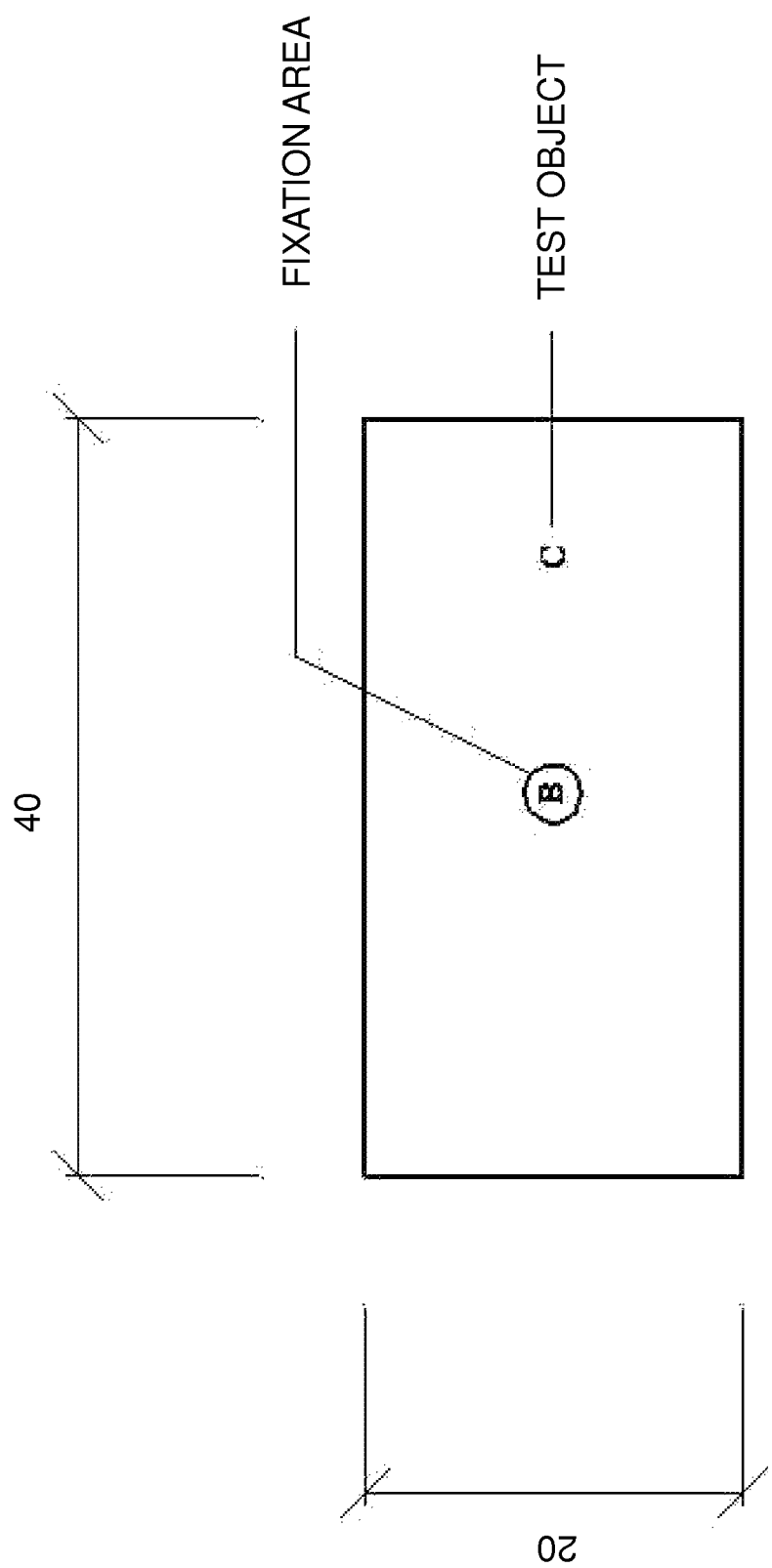
FIG. 6 shows an apparatus for investigating horizontal paracentral scotoma.

Normal reading could be difficult if the patient has paracentral scotoma in a horizontal line 2 degree high and 4 degree long around the center. To test for these paracentral scotoma in this area, the system may display 10 or more different characters without a ring, one at a time at different places in the area together with different characters in the fixation area, as shown in FIG. 6.

FIG. 7 illustrates a program using one or more other examination points. In this embodiment, a computer-implemented testing system is provided run by a program, which controls the system to display one, two or three points in a random or unpredictable (by the testing subject) manner in the fixation area. The patient has to tell, print or place in a digital system how many points in all are in the fixation area, together with one or more examination-points.

FIG. 8 illustrates a system run by a program in which, inside the ring in the fixation area, a dot blinks at different times. After the last blink the examination object is shown. Instead of a blinking dot some numbers could be shown counting up or down.

Using lenticular cards, the examiner can monitor the patient and control the patient's stable central fixation. The examiner or the patient can hold the card so that the examiner can see the patient's eye or eyes. For controlling and registration, the correct patient's answers for a respective lenticular unit can be placed on the rear side of the unit, providing the examiner information simultaneously with the test shown for the patient.

Specialized Examination Objects

The examination objects may be constructed for targeted use in clinical examinations of visual functions. Examination objects can be shown in different sizes, colors or contrast to the background. The test can be performed with static or movable objects. To test the patient's cooperation, sometimes only points or numbers in the fixation area are shown or only examination point(s) in the visual field.

Figure 11B:
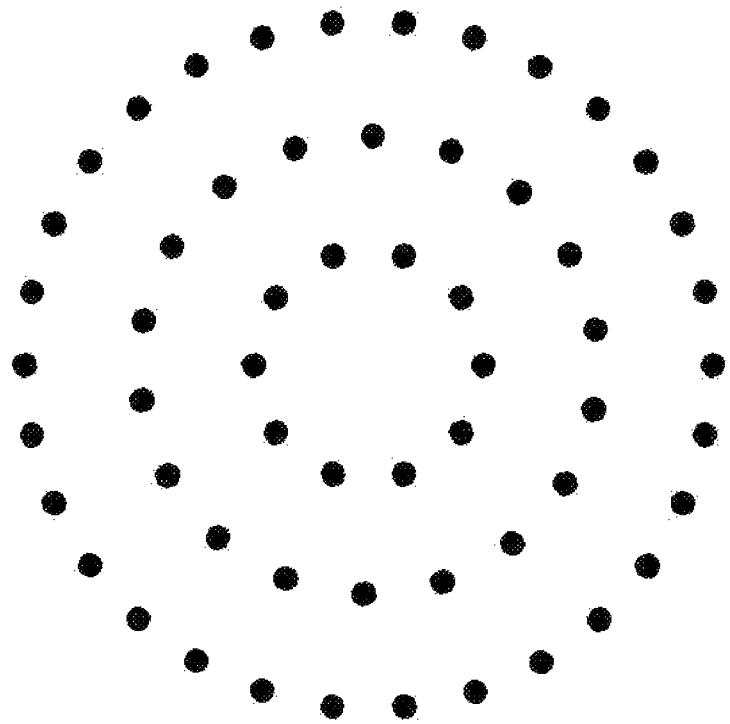
FIG. 11B shows an examination object consisting of dots arranged in a circular manner.
Figure 11A:
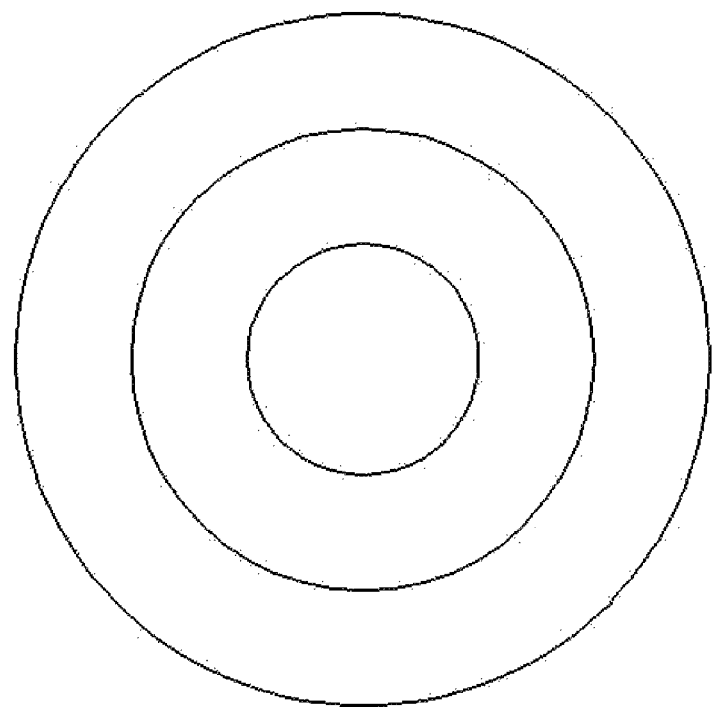
FIG. 11A shows an examination object consisting of rings.
Figure 12:
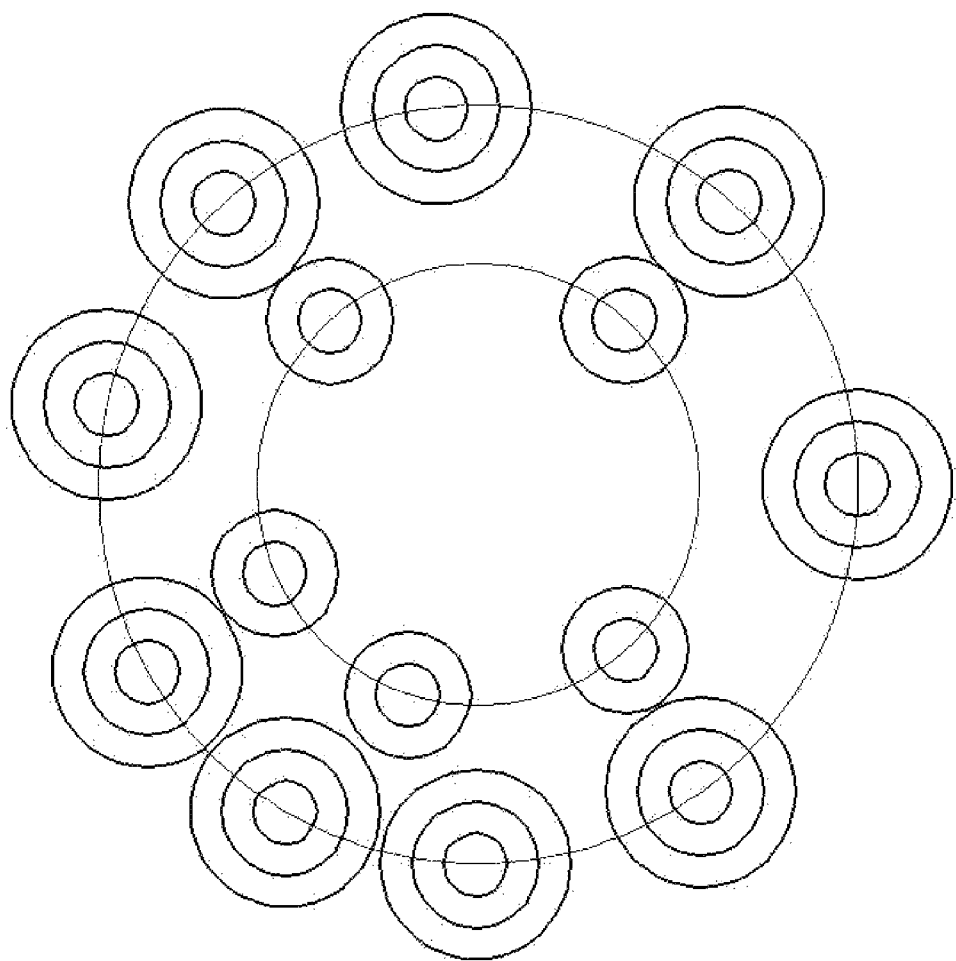
FIG. 12 shows a fixation area displaying examination objects different places in circles around the center.
Figure 13B:
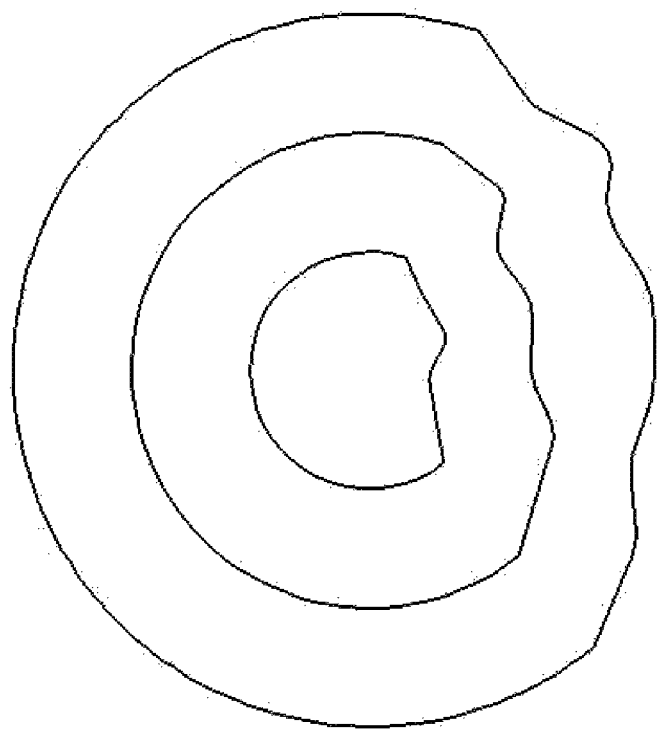
FIG. 13 illustrates scotoma and metamorphopsia.
Figure 13A:
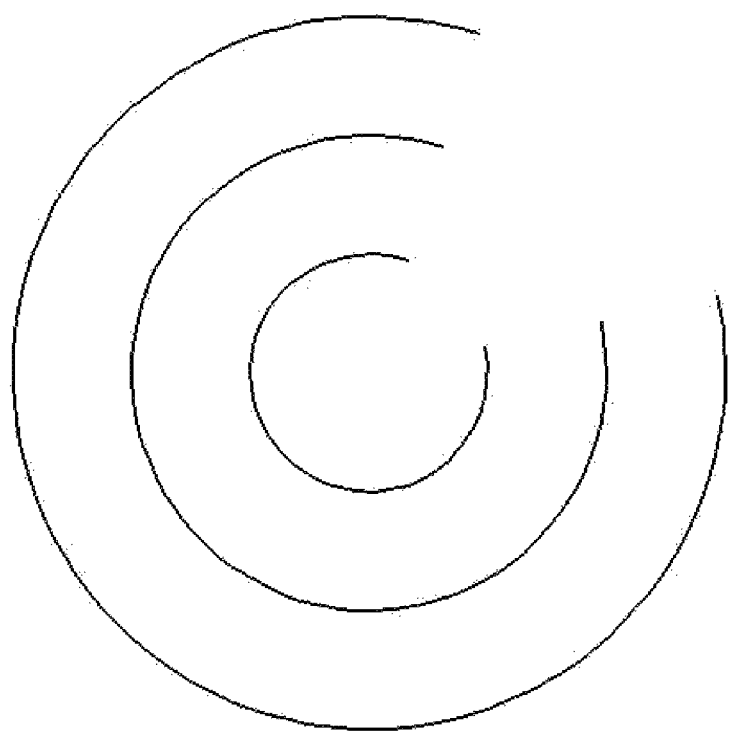
Figure 14:
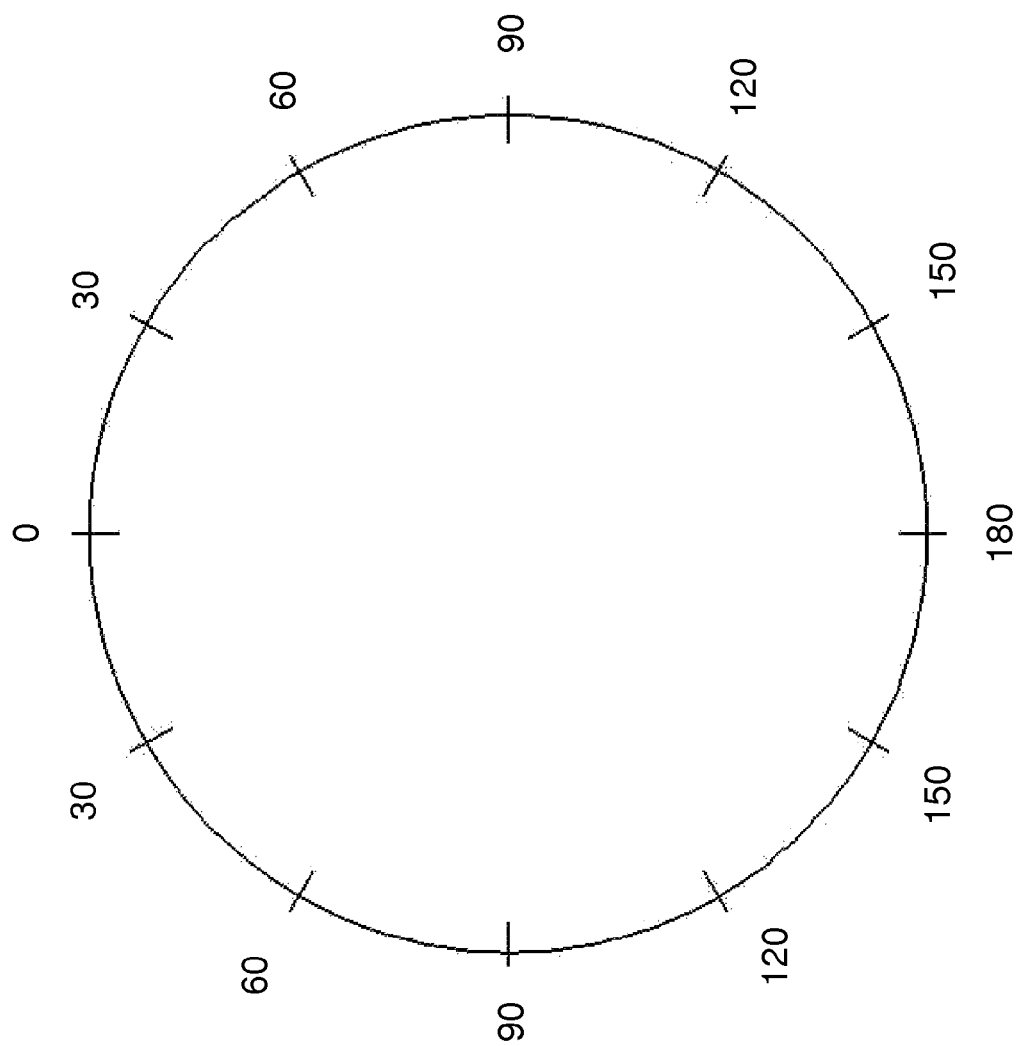
FIG. 14 shows a scale showing the position in degrees from the vertical position.

Specialized objects may be used together with the objects for attention of the fixation area:

1. Test for scotoma: A circular ring with a number or character inside the ring (FIGS. 4-5) is displayed in different sizes, different thickness of the ring and different numbers and characters, different contrast to the background and different colors. Together with the fixation area mentioned in FIGS. 4-5 and FIGS. 7-8, circular dots could be used.
2. Test for metamorphopsia and scotoma: These examination objects are special for monocular tests. FIG. 9 illustrates an examination object consisting of a line (thickness 0.1-0.3 mm, length 20-100 mm) and, parallel to this in a distance of 3-5 mm, a row of circular dots (diameter 0.1-0.3 mm and the same distance between dots, length 20-100 mm). The line and the row of dots can be used with different contrast to the background and with color. The examination object could be presented in horizontal or vertical position. As shown in FIG. 10 the patient has to observe something missing of the line or/and dots (scotoma) and somewhere the line or/and the row of dots are bending or deformed (metamorphopsia).
3. FIGS. 11A-11B Illustrate a examination object consisting of 2 and 4 concentric rings (thickness 0.1-0.3 mm) or circular rings consisting of dots (diameter 0.1-0.3 mm) and with distance between the rings of 3 to 5 mm. The examination object consists of only rings or rings of dots or a mixture and all the rings could have the same or different contrast to the background or the same color or different colors (e.g., Red-Green-Blue) for testing different sensitivity of functional changes in the visual field. The examination object could be presented in different places in the visual field as shown in FIG. 12, where the examination object is presented in different places in circles around the center and where the patient has to observe FIG. 13 something missing of the rings (scotoma) or/and are rings or part of rings deformed (metamorphopsia). Using lenticular units, the unit could be rotated clockwise or anti-clockwise, with the unit (FIG. 14) having a scale outside the testing area showing the unit position in degrees from the vertical position. The same sort of scale could be placed on the backside for the examiner's information.

Test Background

The background is non-textured and could be black, different degrees of gray, and of various colors. A rear face for a lenticular unit (FIG. 3) may be white, grey, black or colored and more or less transparent to light. To make the method more sensitive, the background could be populated with visual noise, for example, small black and white spots flickering randomly. In programmable displays, this can be made by a software program and with lenticular cards by using multi-frames cards.

Binocular Function Test

Many apparatus have been developed for testing binocular functions where images are shown stationary or with some moving objects. In WO 03/092482 A1 (Ocular display apparatus for assessment and measurement of and for treatment of ocular disorders, and methods therefor) a first image is displayed to one eye only, and a second, different image, to the other eye only so that the person being examined perceives a composite image including a moving object.

According to one aspect of the present invention, binocular functions may be tested by presenting objects and images for a short time period (0.2-2.0 seconds). The vision from right and left eye is separated using color or polarization methods. Also the separation could be performed with a perpendicular structure, so that the right eye can only see the right part of the lenticular unit, and the left eye only can see the left part. Using lenticular units having 3D or zoom properties may perform special binocular examinations.

The Preferred Embodiments for the System Using Lenticular Cards

The preferred embodiment consists of one lenticular card or two lenticular cards placed back to back. When using two cards, the one side of the unit can be used for examining the right eye and the other side for examining the left eye, or the two cards could have different examination objects or backgrounds.

The lenticular card or cards are surrounded by a plastic film, which can be moved over the lenticular card, or at the same time over both sides of the lenticular cards (FIG. 15). The fixation area is printed on the plastic film. By moving the plastic film the fixation area can be placed in different distances to the examination objects. In that way it is possible to scan the examination area.

On the plastic film, parts are printed with different transparency, colors, polarization and lenticular parts. When moving the plastic film, different parts of the lenticular card could be hidden or exposed. Instructions to the patient can also be printed on the plastic film and hidden or exposed when the plastic film is moved.

The patient observations of scotoma and metamorphopsia of the examination objects can be indicated with a pen directly on the plastic film, so it is possible to have complete marking on the plastic film of all the patient observations. In this case, the plastic film may be removable, and thus the patient observations on the film retained as part of the file.

The preferred supplementary embodiment for the system using lenticular cards is a seesaw device with an axis parallel with the lenticulars of the lenticular card. Lenticular cards can be tilted to an exact inclination angle where the examination objects are shown for a defined time and then the lenticular cards are tilted back to the primary position. The tilting movements can be carried out mechanically or with an electrical system, such as a bimetallic element, memory metal actuator, piezoelectric actuator, or solenoid. Different inclination angles can be chosen. In that way, it becomes possible to compare results of examination data from different examinations of the same patient or with examinations of other patients.

A timer or alarm may be provided with or as part of the system. The periods may be denoted by an audible or visual alarm, or the alarm may change a visibility of a pattern, such as by causing an inclination of the lenticular card or activation of a mechanical or electrical light shutter. In the same way a voice chip system with instructions for the patient can be provided together with the system.

The Preferred Programmable Display for the System

Programmable displays can be correspondingly used according to similar protocols as used with lenticular units, using non-texture background, short presenting time of the examination objects and high attention to the fixation area. In a computerized embodiment, the human interface and timing elements can be fully automated.

The invention may be implemented as a software program for operating a generic device, with the software stored in non-transitory form in a computer readable memory and executed by a programmable processor.

The preferred programmable display can use different programs, which can be stored and the result of the test may be analyzed, stored and showed on the same display, along with instructions for the test. Instructions can also be given vocally by the programmable display system.

The preferred size of the display for the system is 100×100 mm or more, but smaller displays can be used, when the fixation areas are changed in the program from left-right-up-down, to close to the edge of the display. It is important, that the display has a high-resolution quality. Thus, the display may test a single quadrant of vision, with a fixation area in a corner of the card, thus permitting a 50 mm×50 mm display.

Registration of patient observations can be made on a transparent film over the display or it is preferred to use a programmable electronic display with an overlying touch-screen. This would facilitate patient input of where the examination objects and deformation of examination objects are seen.

A user-facing camera in the programmable display can be used to control the patient attention to the fixation area.

Programmable displays with 3D capability make it useful for binocular test and simultaneously test of both eyes. Preferably, the 3D display does not require special glasses, though LCD shutter glasses may be used.

A 3D viewable electronic display may be provided by placing a lenticular sheet over a display, aligned such that alternate columns of pixels are directed by the lenticular sheet to the right and left eyes, respectively, at a define viewing distance range. In this case, the display remains normal to the viewing axis at all times, and changing the electronic information delivered to the display alters the images presented to each eye. Since the standard Amsler display is 100×100 mm, this permits a relatively inexpensive display system (using the standard Amsler size or larger), similar to an electronic photo frame, which indeed can be programmed to display a series of compressed digital images (e.g., JPEG) at a controlled rate. Therefore, few if any modifications other than the addition of an appropriate lenticular lens sheet over the display are necessary to obtain an electronic display unit according to the present technologies. The electronic display can be programmed according to various testing paradigms as required to present and/or fully administer the test. A more advanced controller, such as a smartphone, tablet, netbook or notebook computer, could be programmed to provide other features, such as adaptive testing in order to fully define any deficiencies, while avoiding excess testing for normal areas of the visual field. Thus, according to one embodiment, an Apple iOS 5 applet or Android 2.3 or 3.1 applet could be created to implement the examination on a smartphone or tablet device. In some cases, a 3D-type display may be provided on a programmable display device, to provide a dynamic examination system with binolcular discrimination.

With programmable displays, all methods for separating vision from right and left eye could be used for testing binocular function and by alternating special examination objects for the right and left eye, both could be examined. A pair of displays may also be provided.

The system using a programmable display is well suited for self-test.

The present technology provides in various embodiments a number of useful features:

Using movable lenticular cards or programmable displays to obtain short presenting time (0.2-2.0 seconds) of examination objects for both monocular and for binocular testing.

Testing for both scotoma and metamorphopsia in the central visual field.

Registering patient observations on supplementary parts in front of a lenticular card or a display or registration on a touch-screen.

Presenting fixation area with higher attention.

Presenting specialized examination objects.

Incorporating supplementary embodiments for tilting lenticular cards to an exact inclination angle and observation time.

Portable system.

Offering flexibility to be used by eye care professionals and for self-test.

Description of the Course of Examination

Most patients prefer testing at their normal reading distance (about 350 mm). When the patient wears his or her eyeglasses or reading glasses, blurring of examination objects could be avoided.

The examination may be performed under the guidance and observation of a skilled person, or the patient may learn how to perform the examination. The system, e.g., lenticular card or display, is held at the distance from the eye and in the orientation, which have been indicated for the system. A fixture may be provided to assist in positioning. In case of monocular examination, generally first the right eye and then the left eye are examined.

In examinations with systems where the right eye and the left eye are presented with examination objects of different colors or light polarizations, the patient has to use eyeglasses having different colors or different light polarizations for the right eye and the left eye to distinguish these objects.

At the beginning of the examination, the patient is instructed to observe specific changes of the examination objects in the form of objects being missing or being seen weakly, in the form of lines or rows of small objects being seen curved, wavy or with bends. If the patient discovers some of these changes, then the patient or an assistant as instructed by the patient may mark these changes directly on the system, on a transparent plate which covers the unit completely or partly, or mark the changes on a form at the side of the system.

Various aspect of the technology may be implemented on an automated computer using known components. The computer may be controlled in accordance with a tangible computer-readable medium, such as a magnetic disk, optical disk, flash memory, and other physical systems. The automated computer itself typically comprises a processor, which may be CISC, RISC, SIMD, multicore, ARM, Intel architecture, or other types.

Embodiments hereof may be implemented as a method, apparatus, or article of manufacture using standard programming and/or engineering techniques to produce software, firmware, hardware, or any combination thereof to control a computer to implement the disclosed embodiments. The term "article of manufacture" (or alternatively, "computer program product") encompasses a computer program accessible from any computer-readable device, carrier, or media. For example, computer readable media can include but are not limited to magnetic storage devices (e.g., hard disk, floppy disk, magnetic strips, etc.), optical disks (e.g., compact disk (CD), digital versatile disk (DVD), BlueRay disks, etc.), smart cards, and flash memory devices (e.g., card, stick). Additionally it should be appreciated that various types of information can be communicated using a carrier wave such as those used in transmitting and receiving electronic mail or in accessing a network such as the Internet or a local area network (LAN). In some cases, these carrier waves reside within tangible media, and can be deemed non-transitory. Of course, those skilled in the art will recognize many modifications may be made to this configuration without departing from the scope or spirit of the disclosed embodiments.

Referring now to FIG. 15, there is illustrated a block diagram of a computer operable to execute the disclosed architecture. In order to provide additional context for various aspects disclosed herein, FIG. 15 and the following discussion are intended to provide a brief, general description of a suitable computing environment 1100 in which the various aspects can be implemented. While the one or more embodiments have been described above in the general context of computer-executable instructions that may run on one or more computers, those skilled in the art will recognize that the various embodiments also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 15, the exemplary environment 1100 for implementing various aspects includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies. Other external drive connection technologies are within contemplation of the one or more embodiments. The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as magnetic hard drives, flash memory cards, optically readable media, and the like, may also be used in the exemplary operating environment, and further, that any such media may contain non-transitory computer-executable instructions for performing the methods disclosed herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. It is appreciated that the various embodiments can be implemented with various available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, a remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an interface, etc.

A monitor 1144 or other type of display device is also connected to the system bus 1108 through an interface, such as a video adapter 1146. In addition to the monitor 1144, a computer typically includes other peripheral output devices (not shown), such as speakers, printers, etc.

The computer 1102 may operate in a networked environment using logical connections through wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adaptor 1156. The adaptor 1156 may facilitate wired or wireless communication to the LAN 1152, which may also include a wireless access point disposed thereon for communicating with the wireless adaptor 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 through the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least IEEE-802.11x (Wi-Fi), IEEE-802.15 (Bluetooth™), and IEEE-802.16 (WiMax) wireless technologies. Thus, the communication can be a predefined structure as with a conventional network or simply an ad hoc communication between at least two devices.

What has been described above includes examples of the various embodiments. It is, of course, not possible to describe every conceivable combination of components or methodologies for purposes of describing the various embodiments, but one of ordinary skill in the art may recognize that many further combinations and permutations are possible. Accordingly, the subject specification intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects. In this regard, it will also be recognized that the various aspects include a system as well as a computer-readable medium having computer-executable instructions for performing the acts and/or events of the various methods. In addition, while a particular feature may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising." See, U.S. Pat. No. 7,822,699, expressly incorporated herein by reference.

It should be understood that the various embodiments of the invention may be combined and sub-combined in all possible consistent permutations. The scope of the invention is limited only by the claims, and no disclosed or preferred embodiment should be interpreted as limiting the generality of the invention.

What is claimed is:

1. A system for clinical examination of visual system functioning comprising:
 a movable lenticular unit comprising a fixation area and one or more lenticular plates configured to project images of a plurality of different examination objects to a viewer dependent on an orientation of the lenticular unit with respect to the viewer gazing toward the fixation area; and
 a holding part configured to orient and maintain an orientation of the lenticular unit in desired orientation with respect to the viewer, such that the respective examination object remains projected on the retina of the viewer while the viewer gazes toward the fixation area during the clinical examination.

2. The system according to claim 1, further comprising at least one supplementary part configured to visually present an object having a predetermined position with respect to the lenticular unit.

3. The system according to claim 1, wherein the lenticular unit comprises a plurality of lenticular plates, each of the plurality of lenticular plates having a distinct lens structure.

4. The system according to claim 1, wherein the examination objects comprise a plurality of unique graphic icons.

5. The system according to claim 1, further comprising an optically polarized plate, disposed between the viewer and the lenticular unit.

6. The system according to claim 1, wherein the fixation area has a predetermined position with respect to the examination objects in respectively different relative orientations of the lenticular unit with respect to the viewer.

7. The system according to claim 1, wherein the examination objects are provided in at least two different colors, further comprising a set of color filter glasses for the viewer corresponding to at least two different colors.

8. The system according to claim 1, further comprising eyeglasses having different light polarization for the right eye and the left eye of the viewer.

9. The system according to claim 1, further comprising polarization filters, which are arranged such that the light projected to the viewer from the fixation area is not polarized, light projected from a first set of examination objects is polarized in a first direction, and light projected from a second set of examination objects is polarized in a second direction, and that eyeglasses with different light polarization permit visualization of the fixation area and the first set of examination objects by the left eye, and the fixation area and the second set of examination objects by the right eye of the viewer.

10. A method for clinical examination of visual system functioning comprising:
providing a movable lenticular unit comprising one or more lenticular plates configured to project images of a plurality of different examination objects to a viewer dependent on an orientation of the lenticular unit with respect to the viewer whose gaze is directed toward a fixation area;
orienting and maintaining an orientation of the lenticular unit in a desired orientation with respect to the viewer, such that the respective examination object remains projected on the retina of the viewer while the viewer gazes toward the fixation area during the clinical examination; and
receiving a report of the visualization of the examination objects from the viewer.

11. The method according to claim 10, further comprising visually presenting an object having a predetermined position with respect to the lenticular unit.

12. The method according to claim 10, wherein the lenticular unit comprises a plurality of lenticular plates, each of the plurality of lenticular plates having a distinct lens structure.

13. The method according to claim 10, wherein the examination objects comprise a plurality of unique graphic icons.

14. The method according to claim 10, further comprising disposing an optically polarized sheet between the viewer and the lenticular unit.

15. The method according to claim 10, wherein the fixation area has a predetermined position with respect to the examination objects in respectively different relative orientations of the lenticular unit with respect to the viewer.

16. The method according to claim 10, wherein the examination objects are provided in at least two different colors, further comprising viewing the examination objects through a set of color filter glasses corresponding to at least two different colors.

17. The method according to claim 10, further comprising providing eyeglasses having different light polarization for the right eye and for the left eye of the viewer.

18. The method according to claim 10, further comprising arranging polarization filters such that light projected to the viewer from the fixation area is not polarized, light projected from a first set of examination objects is polarized in a first direction, and light projected from a second set of examination objects is polarized in a second direction, and viewing the lenticular unit through eyeglasses with different light polarization which permit visualization of the fixation area and the first examination objects by the left eye, and the fixation area and the second examination objects by the right eye of the viewer.

19. A system for clinical examination of visual system functioning comprising:
a reorientable lenticular unit comprising a fixation area for direction of a viewer gaze, and at least one lenticular plate comprising a plurality of parallel cylindrical lenses, configured to project focused images of each of a plurality of different examination objects on a retina of a viewer, a selection of a respective examination object for projection as a focused image on the retina of the viewer being dependent on at least an orientation of the at least one lenticular unit with respect to the viewer, while the viewer gazes toward the fixation area; and
a holder configured to orient and maintain an orientation of the lenticular unit in desired orientation with respect to the viewer during the clinical examination, such that the respective examination object remains projected on the retina of the viewer while the viewer gazes toward the fixation area during the clinical examination.

20. The system according to claim 19, wherein the reorientable lenticular unit comprises a plurality of lenticular plates, each of the plurality of lenticular plates having a distinct cylindrical lens structure.

\* \* \* \* \*